(12) United States Patent
Stichelbaut et al.

(10) Patent No.: US 7,486,771 B2
(45) Date of Patent: Feb. 3, 2009

(54) PROCESS AND APPARATUS FOR IRRADIATING PRODUCT PALLETS OR CONTAINERS

(75) Inventors: Frederic Stichelbaut, Mazy (BE); Jean-Louis Bol, Genappe (BE)

(73) Assignee: Ion Beam Applications S.A. (BE)

( * ) Notice: Subject to any disclaimer, the term of this patent is extended or adjusted under 35 U.S.C. 154(b) by 0 days.

(21) Appl. No.: 11/477,752

(22) Filed: Jun. 29, 2006

(65) Prior Publication Data

US 2007/0009090 A1   Jan. 11, 2007

(51) Int. Cl.
    *G21K 5/10* (2006.01)
(52) U.S. Cl. ........................................ 378/69
(58) Field of Classification Search ............... 378/57, 378/64, 68, 69; 250/492.1, 492.3; 426/234, 426/240
    See application file for complete search history.

(56) References Cited

U.S. PATENT DOCUMENTS

| 3,452,195 A | * | 6/1969 | Brunner .................. 378/69 |
| 4,066,907 A | | 1/1978 | Tetzlaff .................. 378/69 |
| 6,993,111 B1 | * | 1/2006 | Annis .................... 378/57 |
| 7,197,111 B2 | * | 3/2007 | Rose et al. ............... 378/57 |
| 2005/0058246 A1 | | 3/2005 | Rose et al. ............... 378/69 |

FOREIGN PATENT DOCUMENTS

| EP | 1 464 343 A | 10/2004 |
| EP | 1464343 A1 | 10/2004 |

\* cited by examiner

*Primary Examiner*—Courtney Thomas
(74) *Attorney, Agent, or Firm*—Fitch, Even, Tabin & Flannery

(57) ABSTRACT

Method for irradiating in an irradiation chamber products being stored in the form of pallets or in the form of bulk material in appropriate containers by means of a high energy X-ray beam source including the following steps: placing and arranging the products onto two different levels of products, so that a first set of products is placed on an upper level and a second set of products is placed on a lower level; irradiating both sets of products during a first period of time; submitting the products arranged on the two levels to a switch or transposition, so that the set of products arranged on an upper level is arranged on the lower level and vice versa and irradiating during a second period of time the new arrangement formed of the two transposed sets of products.

20 Claims, 14 Drawing Sheets

PROCESS AND APPARATUS FOR IRRADIATING PRODUCT PALLETS OR CONTAINERS

FIELD OF THE INVENTION

The present invention is related to a process and an apparatus for irradiating products with a high energy radiation beam, in particular low density products conveyed in the form of pallets, or as low density bulk material stored in appropriate containers.

A possible application of such apparatus and process is the sterilization of products such as medical devices.

DESCRIPTION OF THE STATE OF THE ART

Sterilization techniques can be divided essentially into two main groups: sterilization techniques using chemicals, such as ethylene oxide (EO) sterilization processing, or sterilization techniques using radiations.

Among the latter techniques, electron beam may be used, but because of the limited penetration depth in matter of electrons (a few centimeters in unit density material), these are not adapted for the treatment of large volumes such as whole pallets.

A better solution is the use of photons because of their better penetration in the depth of the matter. Among these techniques using photons, again two families can be defined: methods producing gamma rays and methods producing X-rays used for sterilization.

In the case of gamma rays, the radiation source is a radio-active element producing gamma rays, such as Cobalt 60. The main feature of such irradiation is an isotropic distribution of gamma rays produced by the source.

In case of X-rays, the use of an electron accelerator for producing a high-energy electron beam is required. This high-energy electron beam then passes through a foil made of a high-Z metal, therefore producing the required X-rays.

Although, this last method is preferred for safety reasons, i.e. in terms of waste disposal, the main drawback of the use of X-rays is the poor efficiency of the electron/X-ray conversion process.

In the particular case of sterilization of low-density products such as medical devices having typically a density comprised between 0.05 and 0.5 $g/cm^3$ and preferably between 0.1 and 0.2 or 0.3 $g/cm^3$, stacked on pallets, the use of X-rays or gamma rays as radiation beam is required for obtaining adequate penetration. X-rays are preferred over gamma rays because they can be controlled easily, and do not produce waste.

Typically, the product pallets are carrier-trays or supports of 80×100, 80×120 or 100×120 $cm^2$, (depth×width) on which products may be stacked up to 180-200 cm. Products to be irradiated may also be in bulk form, such as powder, grains, stored in appropriate containers such as bags or not.

Indeed, the density of the product to be irradiated is a critical parameter to take into account in order to have an efficient irradiation. The radiation source has thus to be sufficiently energetic so as to penetrate in the core of the product. In practice, the minimum dose delivered by the irradiation system has to be greater than 2 kGy for products like foodstuffs but greater than 25 kGy for products like medical devices, in order to reach sterilization requirements.

To be efficient, the irradiation system has to provide an even exposure of the products. It is generally admitted that this condition is satisfied if the dose-uniformity ratio also known as "DUR", corresponding to the ratio between the maximum dose and the minimum dose, is as low as possible and preferably is below 2.5. Ideally, in a situation where the dose is uniformly delivered, the DUR would be equal to 1.

Furthermore, for products placed on pallets or carriers, having e.g. dimensions of 1.0 m×1.2 m, less than 30% of the X-ray energy is deposited as a dose in the products, the remainder traversing the products being lost. One can therefore define the throughput of the installation as the volume of material per unit time that can be processed up to a given dose. The throughput is accordingly dependent of the rate of effective energy used to irradiate a product.

The conveying or transportation system before the irradiation source can also be divided into two main families.

An important family of irradiation systems is related to translation systems, which use a continuous linear conveying of the products before the radiation source. However, this kind of irradiation systems has the drawback that it requires a shielding in the form of a maze which will need a rather important overall space, and a complex transport system along the maze.

Typically, in these irradiation systems, products are stacked either on pallets or on unique carrier trays and maintained in a storage area ahead of the irradiation chamber before being conveyed past the radiation source for irradiation of at least one of their sides. A second pass of the pallets or carriers may be then planned in order to expose their opposite side to the radiation source.

Examples of said irradiation translations, horizontal irradiation systems are known from WO-A-03/028771, U.S. Pat. No. 5,396,074, EP-A-0999556.

Another family of irradiation systems consists of rotation systems, using means for rotating a pallet or a container of products before the radiation source. These irradiation systems are well described in U.S. Pat. Nos. 4,066,907, 4,018,348 and 6,504,898.

A particular example is described in U.S. Pat. No. 5,001,352 wherein a process and an apparatus for the irradiation are disclosed, whereby the objects are packed in shipping units having a symmetry of axis running parallel to the direction of conveyance or parallel to the longest extension of the source of radiation. Some of the objects are brought to a position near another object and placed at a distance from the source of radiation, so that near objects partially shield the distant objects from the radiation source in such a manner that the shielding effect is less near the axis of symmetry than in the peripheral area. The objects are moved in such a way that they are irradiated from at least two sides.

Although, it is described in particular that the irradiation can be performed either with a X-ray or a gamma-ray source, the fact that there is a rotation according to a central axis of symmetry, the process and the apparatus described in this document will only show a good uniformity of the absorbed radiation if the radiation source consists of a gamma-ray emission source. In the several embodiments, it is mentioned that the source consists of a rod-shaped source made of individual elements consisting of Cobalt 60.

Furthermore, in said document, FIG. 3 depicts a longitudinal view of the apparatus illustrating a carrousel with an overhead platform and a column of objects to be irradiated which are resting on pallets and are deposited on four carrying devices. Accordingly, each object represented in FIGS. 1 and 2 can be replaced by a column of several objects wherein, after irradiation process, the lower shipping unit is removed, then the three remaining units are lowered on one store and finally, an un-irradiated shipping unit is placed on the top store.

U.S. Pat. No. 6,215,847 describes a product irradiator comprising a loading-unloading area and an irradiation chamber, a continuous track having a level-changing portion, wherein the continuous track enters and exits the irradiation chamber from the loading-unloading area. The continuous track is comprised of at least one rail and of at least two levels to about eight levels. An irradiation source, for example cobalt 60, and which is preferably horizontal in orientation, is located within the irradiation chamber. The product irradiator comprises a substantially horizontal carrier, which is engaged to the continuous track and at least one drive mechanism capable of moving the carrier along the continuous track. It should be noted that the translation of the several pallets on the continuous track is performed along one same direction.

EP-A-1 459 770 describes a process and an apparatus for irradiating products by means of a high-energy X-ray beam source suggesting to optimize the throughput of the installation, while maintaining an appropriate dose uniformity ratio by irradiating simultaneously a stack formed of at least two contiguous pallets. More preferably, at least four contiguous pallets are provided on a single same plane. The irradiation is performed with an overscanning of the pallets.

According to a preferred embodiment, these four pallets are placed on a rotating mean, in order to perform a rotation to the whole stack of pallets during irradiation.

If the DUR ratio has been improved along a horizontal plane of the pallets, still the uniformity of this parameter according to the vertical axis is not sufficient.

AIMS OF THE INVENTION

The present invention aims to provide an apparatus and a process for irradiating products, which do not present the drawbacks of the devices and processes of the state of the art mentioned hereabove.

A particular aim of the present invention is to provide an apparatus and a process which allow a uniform irradiation of low density products (densities lower than 0.5 $g/cm^3$) and in particular products such as medical devices having a density lower than 0.3 $g/cm^3$ and requiring an important dose higher than 20 kGray, having a better throughput than state of the art devices.

The present invention also aims to provide an apparatus and a process which allow an irradiation of low density products giving a DUR ratio below 2.5.

The present invention also aims to provide an apparatus and a process for performing secured and reliable irradiation with moderate cost in terms of equipment, as well as in terms of treatment time.

In particular, the present invention aims to provide a process and an apparatus which allow simultaneous irradiation of a great quantity of products maintained on pallets.

SUMMARY OF THE INVENTION

A first object of the present invention is related to a method for irradiating in an irradiation chamber products being stored in the form of pallets or in the form of bulk material in appropriate containers by means of a high energy X-ray beam source, comprising the following steps:

placing and arranging the products onto two different levels of products, so that a first set of products is placed on an upper level and a second set of products is placed on a lower level;

irradiating both sets of products during a first period of time;

submitting the products arranged on said two levels to a switch or transposition, so that the set of products arranged on an upper level is arranged on the lower level and vice-versa;

irradiating during a second period of time the new arrangement formed of the two transposed sets of products.

Preferably, the two different levels consist of two superposed vertical levels.

Preferably, the first period of time and the second period of time correspond, so that the transposition of the two levels occurs in the middle of the whole period of irradiation of said products.

According to a first embodiment, the products are conveyed before the source with a translation conveyor device.

Preferably, the translation conveyor device consists of two independent parallel sub-devices conveying the products on the two different levels.

According to another preferred embodiment, the products are conveyed before the source with a rotating conveyor device.

Preferably, the rotating conveyor device consists of two independent parallel sub-devices conveying the products on the two different levels.

According to a preferred embodiment, the set of products present on each level consists of one pallet or one container.

According to another preferred embodiment, the set of products present on each level is in the form of a stack of at least several contiguous pallets or containers placed in the same plane.

Preferably, the plane is essentially a horizontal plane.

Advantageously, the photon source is a high energy X-ray beam source.

Preferably, the high energy X-ray beam source is directed to the sets of products from substantially mid-height of the lower level up to substantially mid-height of the upper level.

Preferably, the high energy X-rays are obtained by scanning an electron beam along a height essentially corresponding to a distance comprised between substantially mid-height of the lower level up to substantially mid-height of the upper level.

Another object of the present invention is related to an apparatus for irradiating in an irradiation chamber products being stored in the form of pallets or in the form of bulk material in appropriate containers, having at least:

a high energy photon source;

means of conveying said products in front of the source, said means being able to arrange the products in two sets of products, each being placed on a different level, and means for submitting the sets of products arranged on each level to a switch or transposition so that the set of products arranged on the upper level is arranged on the lower level and vice-versa.

Another object of the present invention is related to an apparatus further comprising means for directing a photon beam along a height essentially corresponding to a distance comprised between substantially mid-height of the lower level up to substantially mid-height of the upper level.

SHORT DESCRIPTION OF THE DRAWINGS

FIG. 1 represents a general top view of an irradiation installation, according to one embodiment of the present invention.

FIG. 2a et FIG. 2b represent a general top view and a side view of an irradiation installation, according to a second embodiment of the present invention.

FIGS. 3 and 4 represent two examples of a relative horizontal arrangement of four product pallets as placed on rotating means, according to particular preferred embodiments of the present invention.

FIG. 5 corresponds to a schematic vertical sectional view along the line X-X of FIG. 1 or of FIG. 2 showing the relative arrangement of the electron beam horn, the X-ray target and the pallet to be irradiated.

FIGS. 6 and 7 represent the dose along the vertical axis according to the vertical height of a pallet being treated according to the method of the present invention, after a first pass called the low-pass irradiation and according to a second pass called the up-pass irradiation as well as the total dose received by the pallet for a product having a density of 0.1 g/cm$^3$, wherein the calculation has been performed firstly with a 40 cm air gap between pallets, and secondly with a 15 cm wooden support or tray and 25 cm air gap between pallets, respectively.

Figure 11:
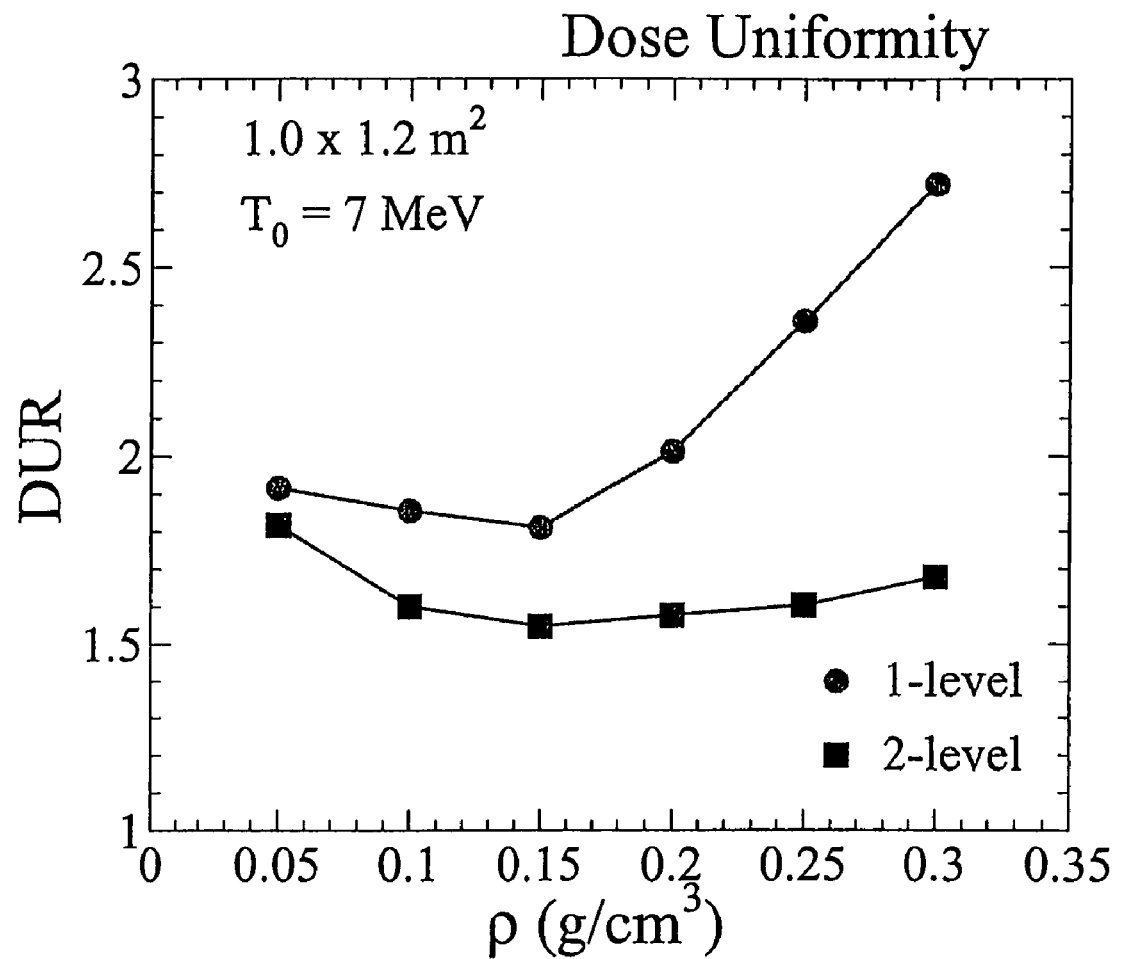

FIG. 11 gives the performance of the DUR ratio, respectively as a function of the density of a product irradiated with an energy of 7 MeV, respectively for the process of the state of the art (represented by dots) compared to the process according to the present invention (represented by squares).

Figure 12A:
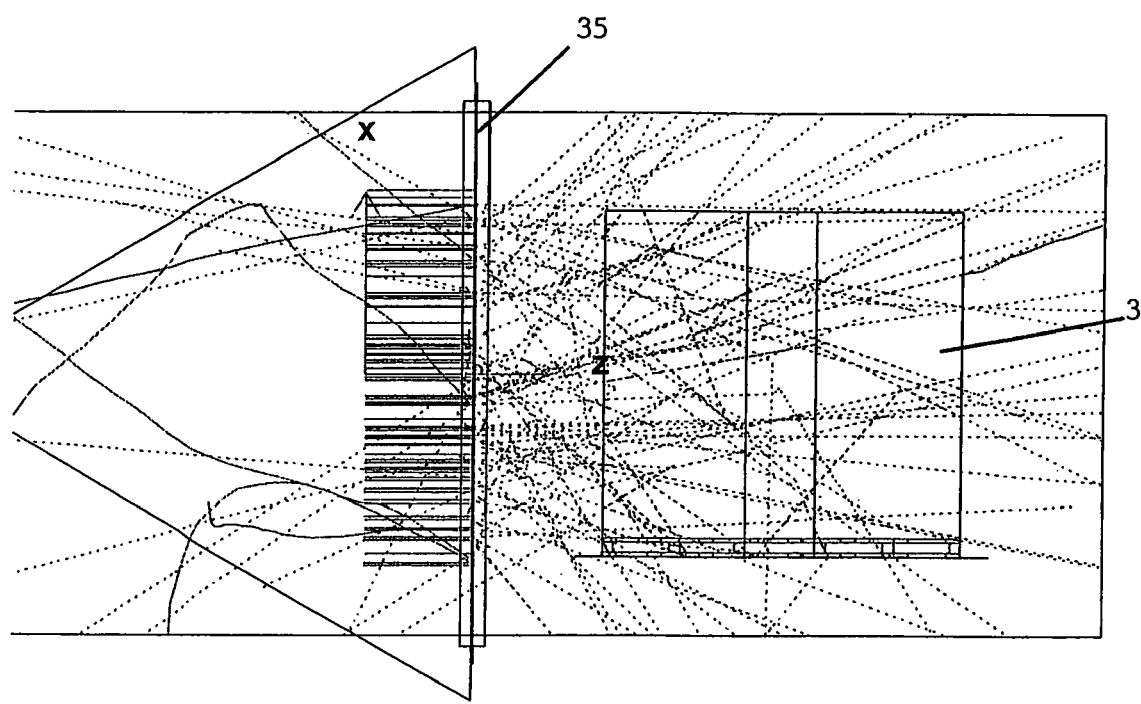
Figure 12B:
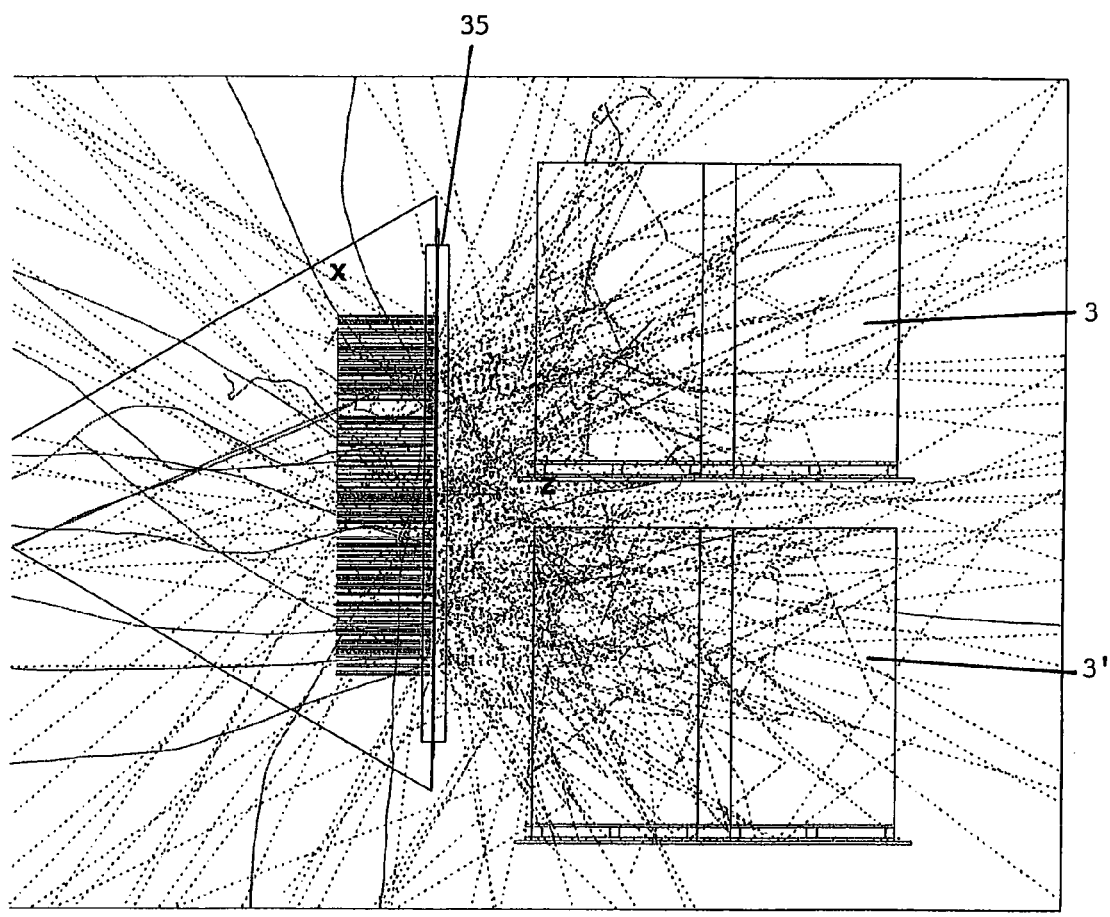

FIG. 12a and FIG. 12b represent a simulation calculated according to the Monte Carlo method of the behaviour of the photons generated on a conversion target by an electron beam produced by a conventional cyclotron for a set of pallet(s) placed on one level according to a sterilization method according to the state of the art (FIG. 12a) and according to a sterilization method of the present invention (FIG. 12b) respectively.

Figure 13:
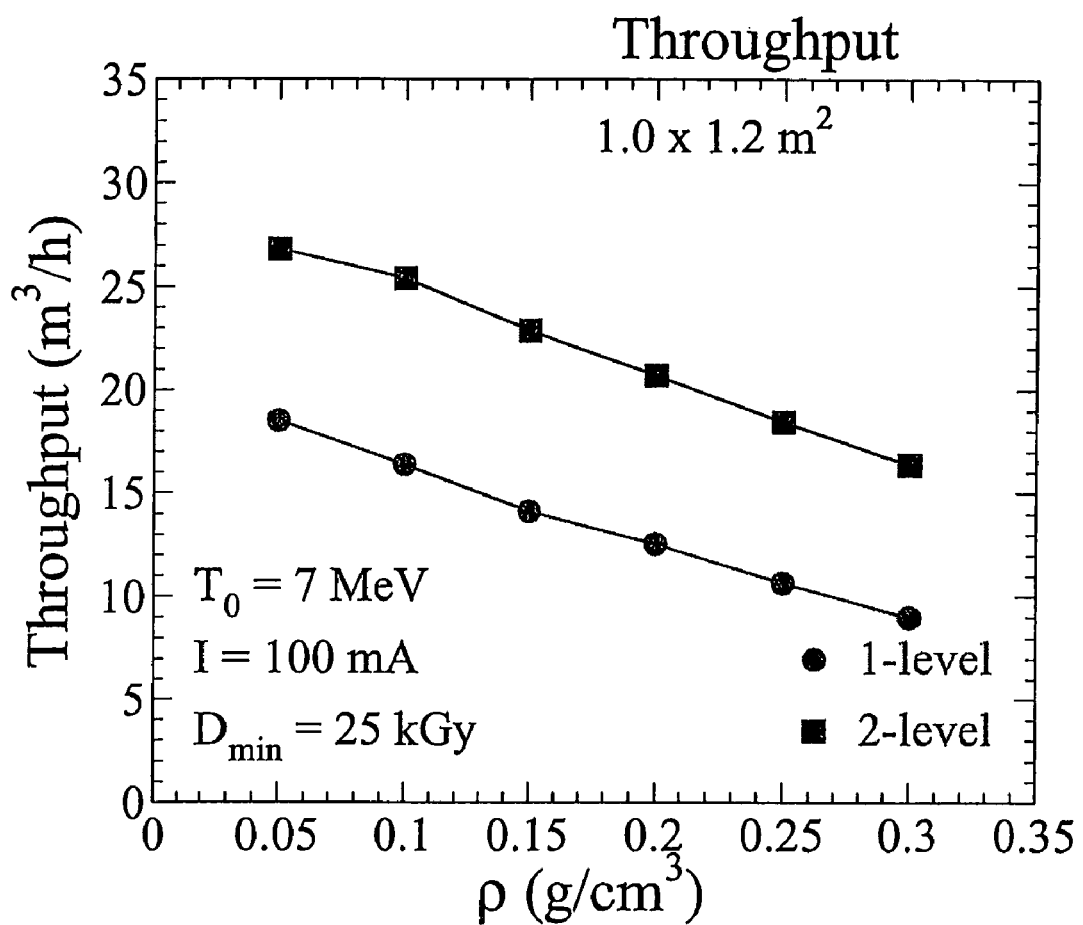

FIG. 13 gives the performance of the throughput, respectively as a function of the density of a product irradiated with an energy of 7 MeV, respectively for the process of the state of the art (represented by dots) compared to the process according to the present invention (represented by squares).

Figure 14:
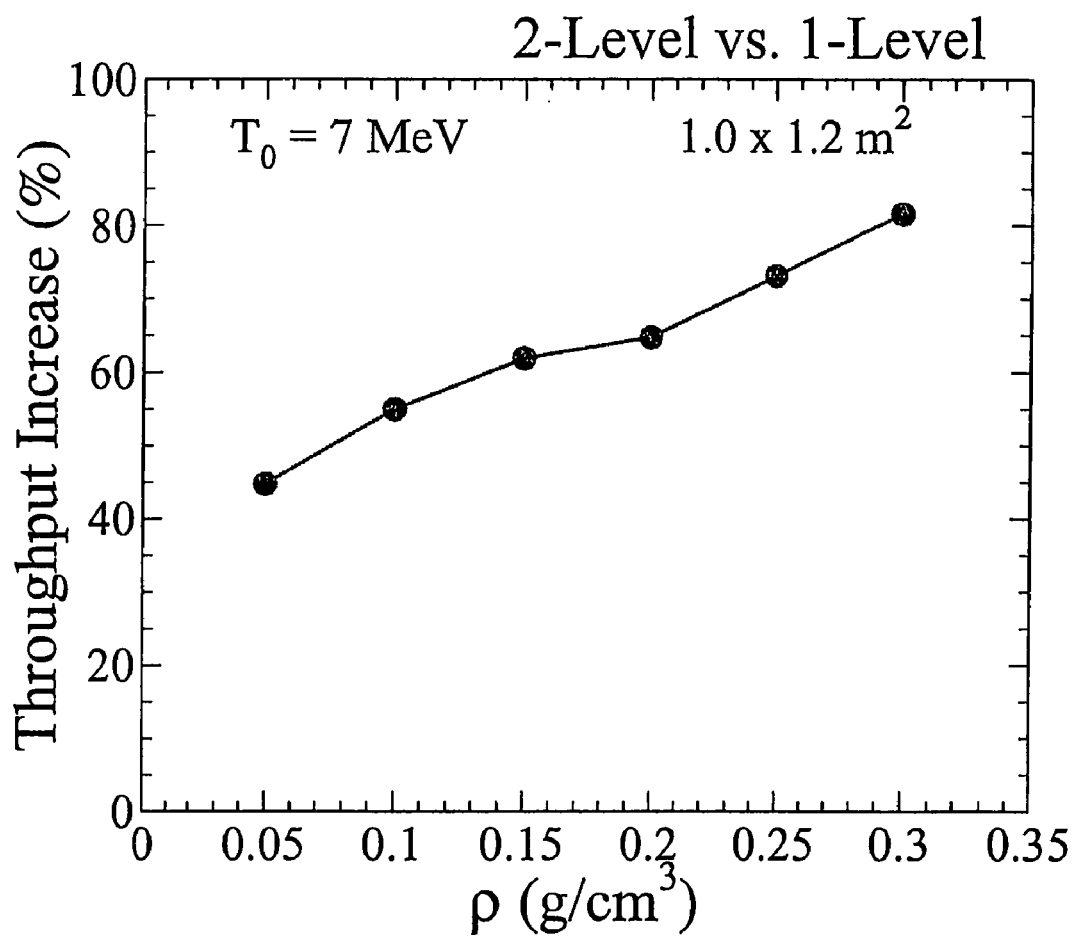

FIG. 14 corresponds to the gain of the throughput as a function of the density of a product irradiated using the process of the present invention.

DETAILED DESCRIPTION OF SEVERAL EMBODIMENTS OF THE PRESENT INVENTION

When irradiating a product set (pallet or container) from the side with an X-ray beam, two considerations have to be taken into account: firstly, in order to achieve effective sterilization, a minimal dose must be deposited throughout the volume of the product set. Owing to the properties of X-rays, dose deposition will not be uniform, and some of the areas will receive a larger dose. This non-uniformity is qualified by the "Dose Uniformity Ratio" (DUR) which is the ratio of the maximal dose deposited in the volume to the minimal dose deposited in the volume. It is desirable that this ratio be as near to one as possible, and preferably below 2.5.

A second consideration in the design of an irradiation system is the throughput of the installation. The throughput of the installation can be defined as the volume of material per unit time that can be processed up to a given dose. This throughput depends on the size of the product set. For smaller sizes, the throughput is low because a large part of the X-ray energy traverses the product and is lost. For larger sizes, a long irradiation is necessary for reaching the minimal dose in the centre of the product set. This leads to a higher dose at the surface of the product set, and hence a higher DUR, and reduced throughput. In between these extremes, an optimal size maximizes throughput.

The idea underlining the present invention is to suggest to superpose on two different levels, products being either in the form of pallets, or in the form of bulk material placed in appropriate containers and to submit them to an irradiation by X-rays during a first period of time, so that irradiation is performed simultaneously for the two superposed levels of products.

In the middle of the treatment, the two levels of products are transposed or switched so that the lower level of products becomes the upper level of products, and vice-versa, then to submit them during a second period of time to irradiation, so that irradiation is performed simultaneously for the two superposed levels of products.

By a transposition or a switch it should be understood a permutation or inversion of the pallets or containers present on each level, wherein the set of products is not reversed. This means that the top or the bottom respectively of the pallet or container remains the top or the bottom respectively of the pallet or container during the permutation and afterwards during irradiation.

This process can be applied either to translation conveying systems or to rotating conveying systems.

Figure 1:
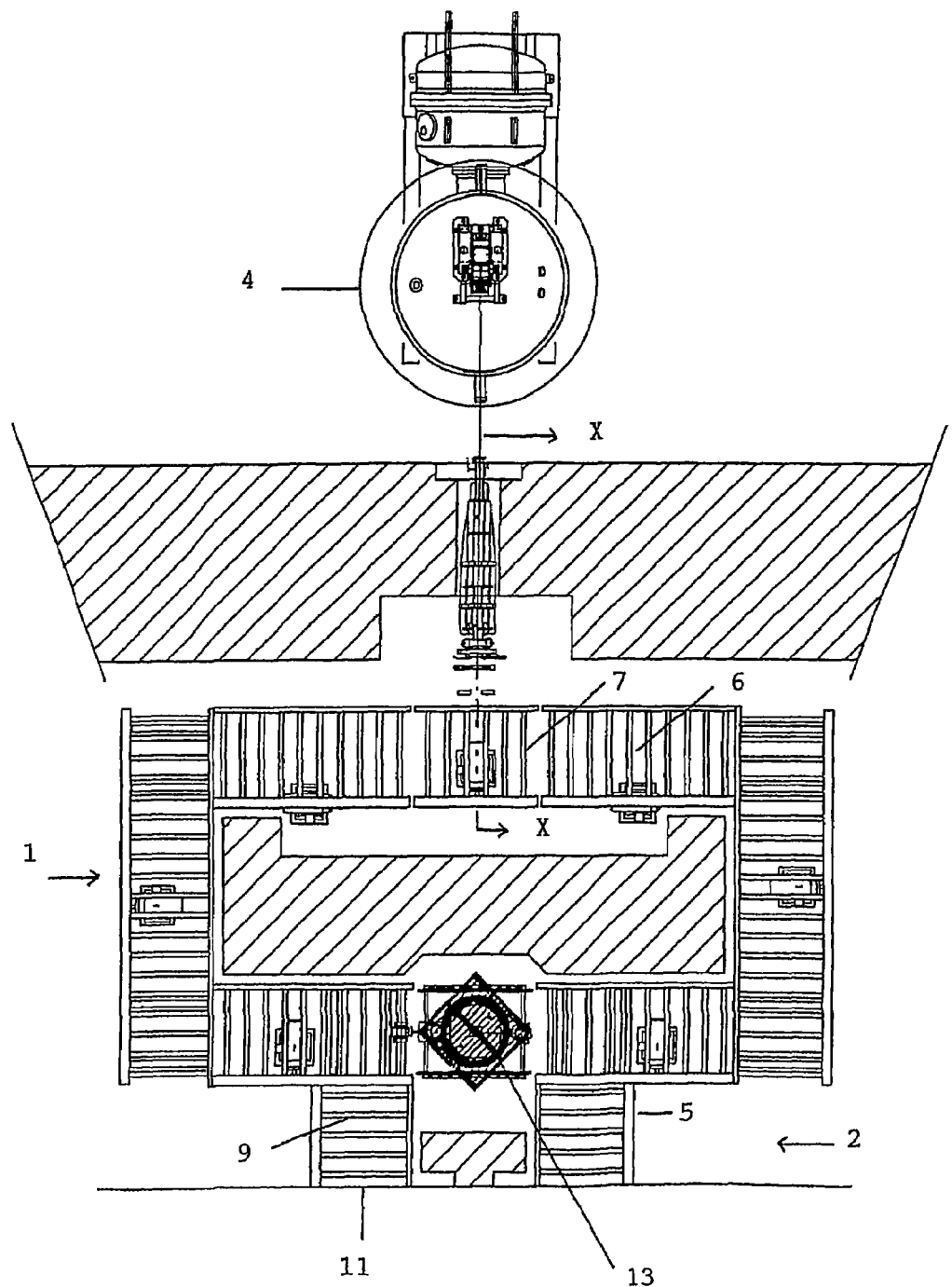

According to a first embodiment, wherein it is suggested to use translation transportation of the products before the source, the installation is described as a top view in FIG. 1. It should be understood that according to said embodiment, the conveyor translation system is divided into two parallel conveying systems (an upper conveying system and a lower conveying system), so as to transport the products on an upper level through a conveyor 2 and on a lower level through a conveyor 2.

The apparatus comprises an irradiation chamber 1 where irradiation takes place and classical conveying means 2 or 2' to bring pallets or containers supporting the products in front of the radiation source 4 in said irradiation chamber 1. The circuit of each conveyor system 2, 2' is divided into several portions, corresponding to loading (5), accumulation (6), exposure (7), control (8), and unloading portions (9).

More precisely, if the set of products have been sufficiently irradiated according to specific predetermined requirements, they are driven onto a portion of the circuit corresponding to an unloading portion (9) along which the products go out of the irradiation chamber 1 (through exit 11) and are unloaded. If the set of products has been insufficiently irradiated, it can be transferred into a portion which is the reorientation portion 10 where sets of products are reoriented e.g. by a 180° rotation, in order to expose the opposite side to the irradiation (2 pass process) or by a 90° rotation (4 pass process) along the vertical axis e.g. using rotation means 14 and then transferred to the accumulation portion 6 in order to pass again in front of the radiation source 4.

As already mentioned, the pallets or containers have to be transposed from the lower level to the upper level for the lower set of products and from the upper level to the lower level for the upper set of products. This is performed through appropriate means such as lifting means. The lifting means can also be associated with the reorientation means 13.

Advantageously, the combination of the horizontal movement of the set of products along the conveying system 2 or 2' before the radiation source 4 and the vertical scanning of the photon beam will impose a full 2D design to the irradiation of the set of products.

Figure 2A:
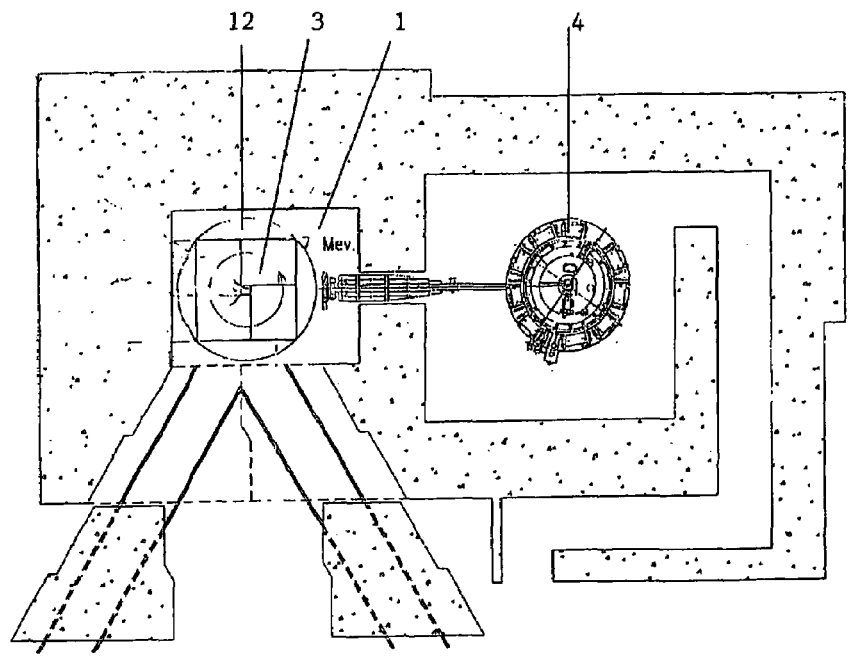
Figure 2B:
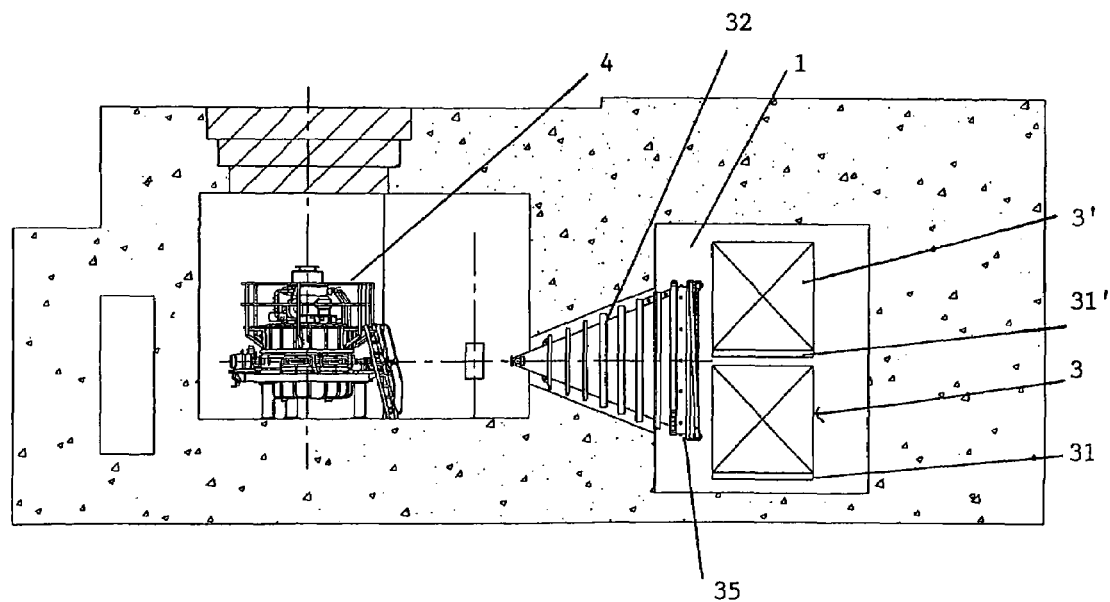

According to another preferred embodiment, wherein it is suggested to use a rotation transportation of the set of products before the source, the installation is described as a top-view in FIG. 2. Said apparatus shown in FIG. 2 comprises:
- a protective shielding;
- a source 4 able to emit a high energy electron beam, said electron beam being directed to a foil of high-Z material 35 for producing X-rays;
- an irradiation chamber 1 where irradiation may take place;
- rotation means 12 included inside the irradiation chamber 1 and located in front of the radiation beam source 4.

Preferably, each of the rotation means that are present on each of the level are capable of carrying a set of products to irradiate and rotate this set (one or more pallets or one or more containers) in front of the irradiation source.

Preferably, said products are placed before the source in a stack of products comprising at least two contiguous pallets placed in the same horizontal plane on each level.

This means that the products are rotated in such a way that they do not rotate relatively with respect to each other. They are rotated and irradiated as a whole.

Thereby, the set of products is irradiated as a stack from the lateral side.

According to another preferred embodiment, the pallets or containers can be rotated individually and/or around a centrally placed gamma source, such as a Cobalt 60 source.

According to another embodiment, the rotating means of the apparatus on each level is adapted to carry one single container, containing products in bulk. This container may have a cylindrical form with an inner wall and an outer wall, wherein the products in bulk are present in the space between the two walls thereby creating an empty column in the centre of the container. The effect of the empty column is to optimize the dose uniformity in the same way.

The rotation means may comprise a turntable, but could be any other suitable rotation means.

The method and apparatus of the invention allow a number of pallets or containers to be irradiated simultaneously as two horizontal stacks present on two different levels by successive penetration of the beam into each pallet or container of the set of pallets or containers arranged before the source.

Figure 3:
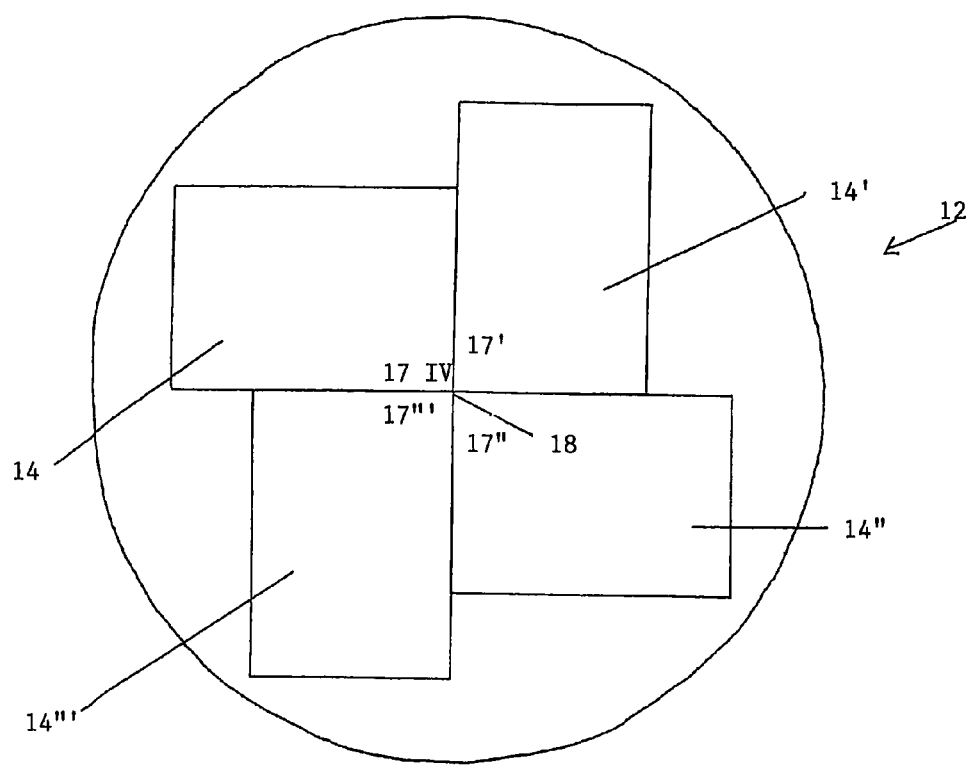
Figure 4:
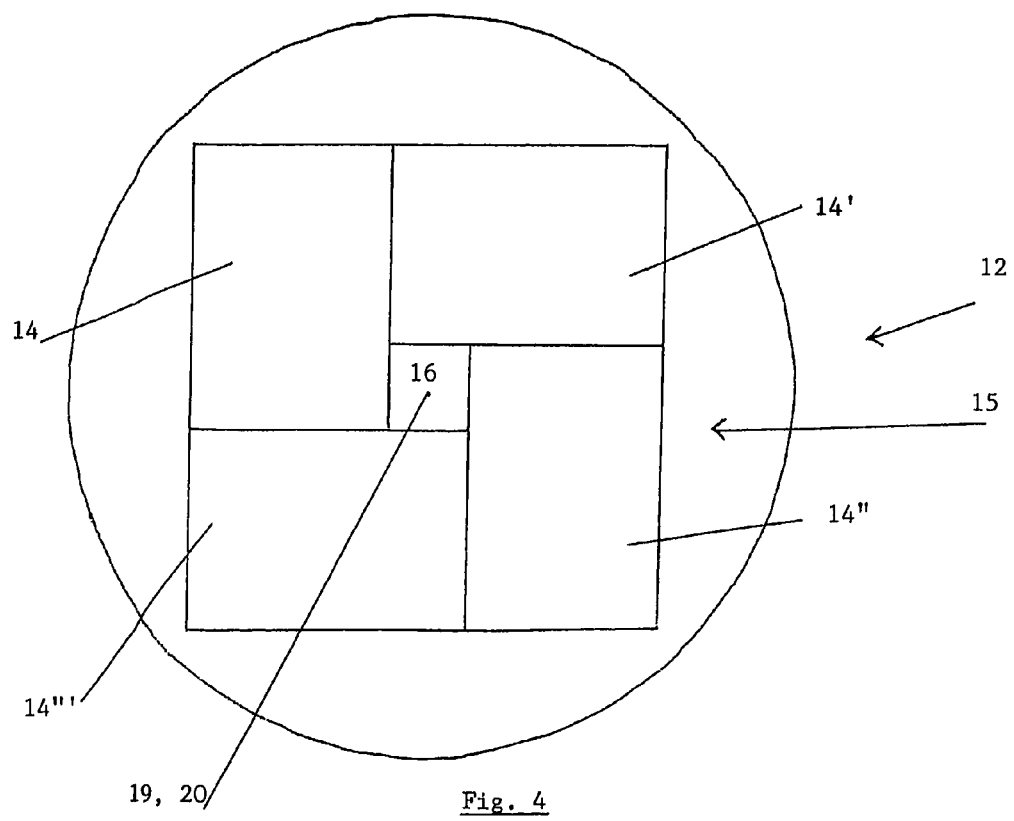

Two examples of a preferred arrangement of these stacks are shown on FIGS. 3 and 4, wherein four rectangular based product pallets 14, 14', 14", 14''' are placed as product stack on the turntable 12 in a same plane B, which is parallel to the plane A of the turntable 12. According to a first preferred embodiment as in FIG. 3, the four pallets 14, 14',14", 14''' are arranged relatively to each other to form together a square base 15 with an open column 16 at the centre 19 of the square. Preferably, said centre 19 coincides with the centre 20 of the turntable 12. One advantage of said configuration is that the problem that the products receive a dose higher than required—a problem associated to classical irradiation apparatus—is avoided here, as the area where this over-irradiation occurs precisely corresponds to the whole or open column 16, where there is no matter.

An alternative possible embodiment for arranging four pallets as a horizontal stack on the rotation means (turntable) 12 is illustrated on FIG. 4. In said embodiment, one defines for each pallet 14, 14', 14", 14''' one corner 17, 17', 17", 17''' respectively and the pallets are arranged so that said corners 17, 17', 17", 17''' coincide with each other at a contact point 18. Preferably, said contact point 18 coincides with the centre 20 of the turntable 12.

Figure 5:
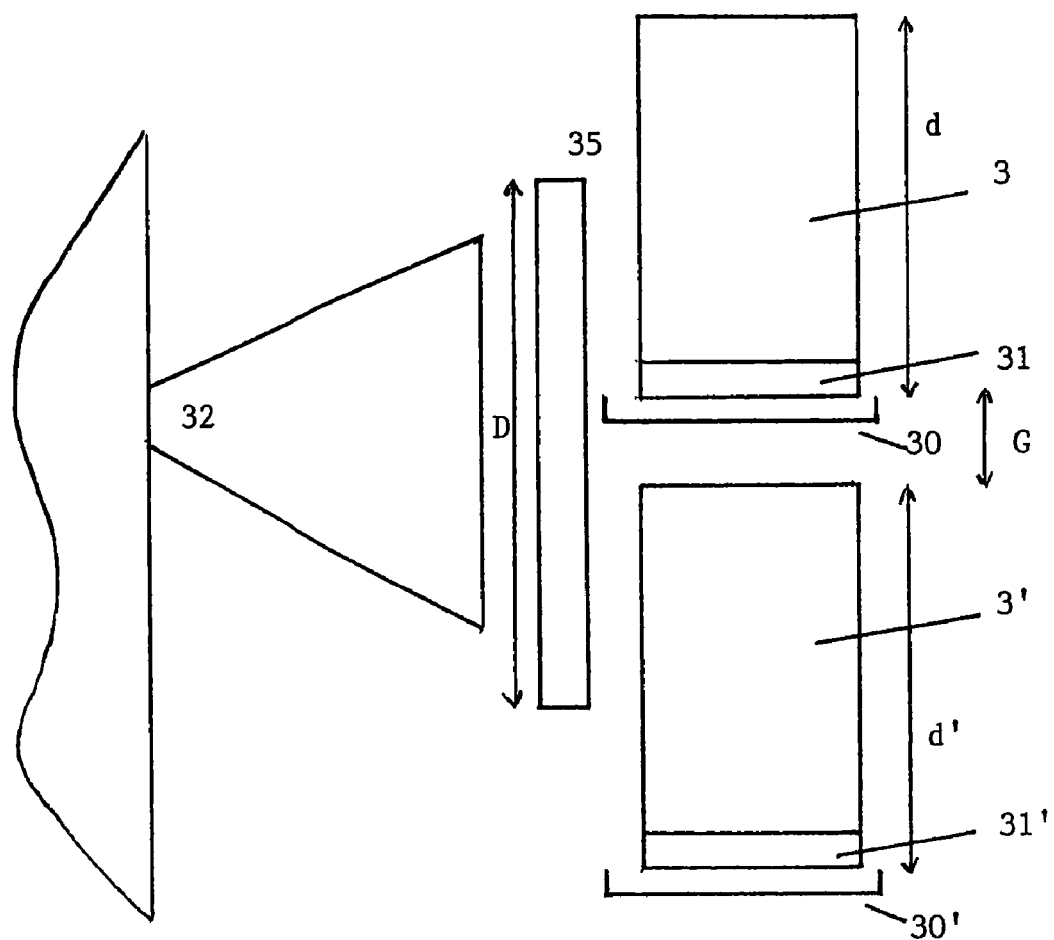

FIG. 5 is representing a side view of the specific configuration of the superposition of two sets of products (in this case two pallets 3 and 3' of products) on two different levels in front of the source 4.

As illustrated on FIG. 5, the radiation source 4 preferably comprises an electron beam source or e-beam horn 32 which irradiates an X-ray target 35 which generates an X-ray beam (photon beam) for product irradiation.

Each set of products is placed either on a translation conveyor or on a turntable (schematized by the reference numbers 30 and 30') and is submitted to the X-ray irradiation.

Preferably, the high energy X-ray beam source is directed to the sets of products from substantially mid-height of the lower level up to substantially mid-height of the upper level. Accordingly, the high energy X-rays are obtained by scanning an electron beam along a conversion target, on a height extending essentially from a distance comprised between substantially mid-height of the lower level up to substantially mid-height of the upper level.

This means that preferably, the total diameter of the end of the e-horn (D) is calculated as to be equivalent to twice half of the total height (d) of a pallet plus the gap present between the two levels on which the pallets are positioned:

$$D \simeq 2d/2+G=d+G$$

Thereby, no overscanning of the pallets is performed.

Because of this specific configuration, the same pallet being submitted to a first pass defined as the lower pass, wherein the pallet is positioned on the lower level, and to a second pass defined as the upper pass, wherein the pallet is positioned on the upper level, will show a rather even exposure on the whole height of the pallet. The dose has been calculated for an irradiation of products having a density of 0.1 g/cm$^3$, without any wooden support and an air gap of 40 cm (see FIG. 6) and with one pallet positioned on each level with a 15 cm wooden support and an air gap of 25 cm in between (see FIG. 7).

In the second case, which is, of course, the real working condition, one observes a small decrease at the bottom of the pallets. This is due to the fact that the wooden support or tray will absorb a non-negligible dose during irradiation. However, this effect is compensated in the present case compared to the process according to the state of the art (one pass with overscanning).

By irradiating essentially one half of the pallet during the first time period of the process, e.g. the upper half for the pallet placed on the lower level and the lower half for the pallet placed on the upper level, and interchanging the pallets so that it is the other half which is essentially irradiated during the second time period, a part of the created photons will be scattered to the half not treated, e.g. the lower half for the pallet placed on the lower level and the upper half for the pallet placed on the upper level, and this during both periods of time. Because of a better efficiency of the use of x-rays, the throughput will accordingly also be improved.

Figure 6:
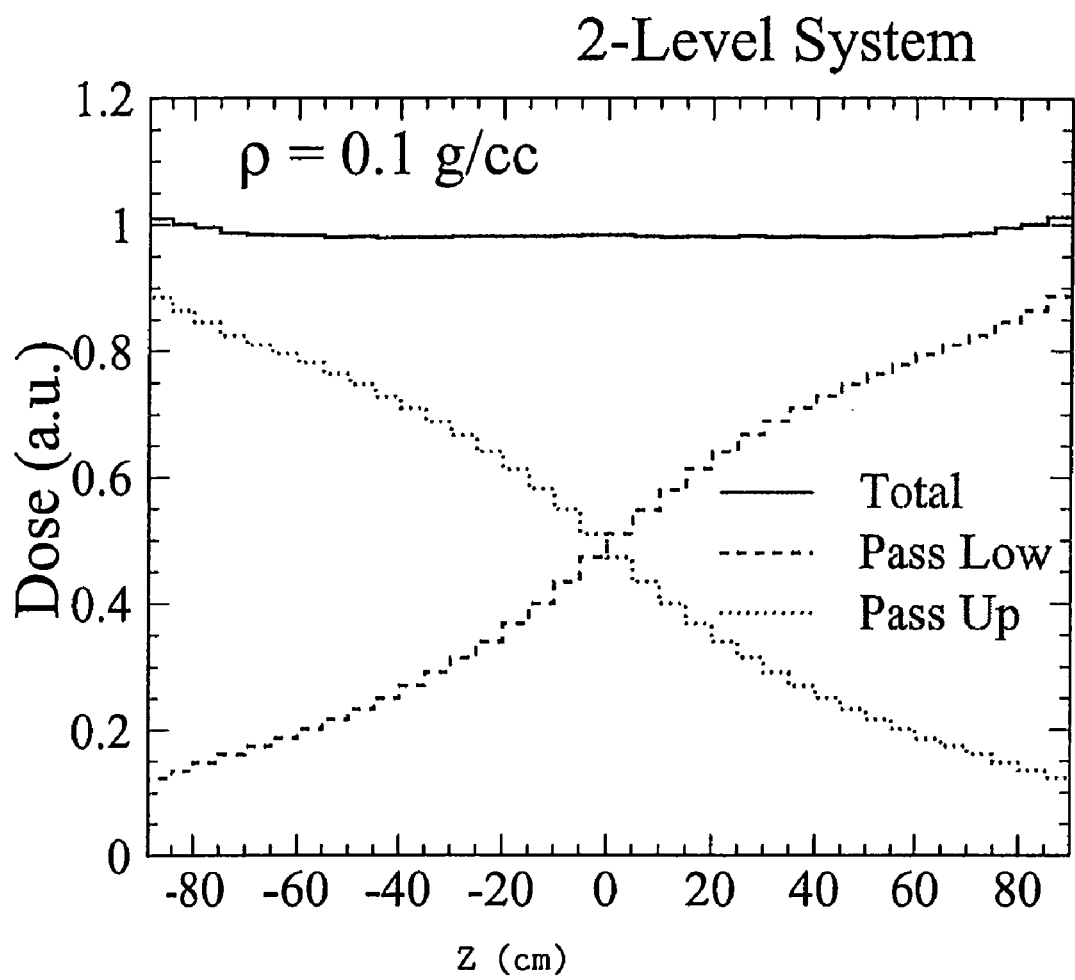
Figure 7:
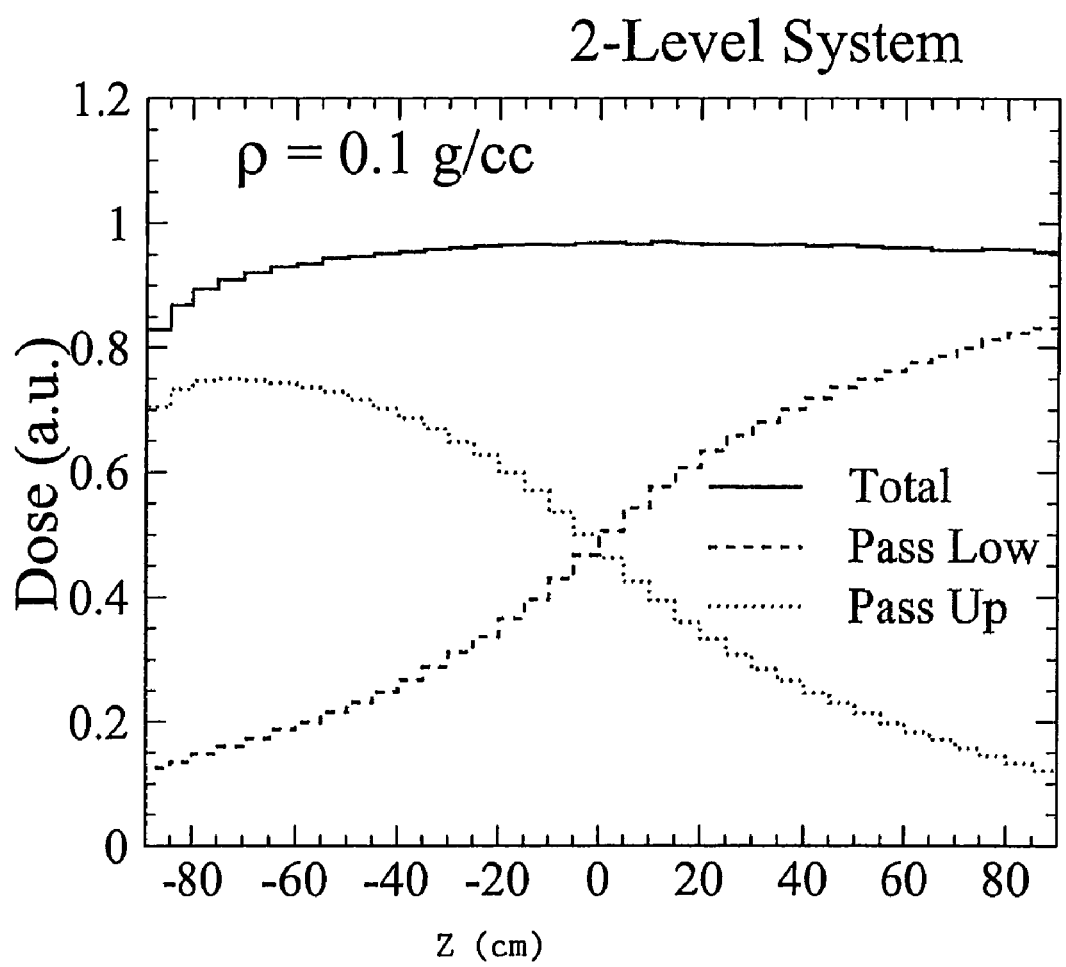

In FIGS. 6 and 7 and in the following, the measurements have been performed according to the height (Z) of a pallet, 0 representing the median height, (−80) the bottom and (+80) the top of the pallet.

FIGS. 8a, 9, 9a and 10a represent products having a density of 0.1 g/cm$^3$, 0.2 g/cm$^3$, 0.3 g/cm$^3$ respectively, the minimum dose rate (Dmin) and the max dose rate (Dmax).

The minimum dose rate corresponds to the dose delivered so that the product is submitted to a sterilization, which corresponds to an irradiation of at least 20 kGy.

The maximum dose is the maximum dose delivered to the product.

The important parameter to follow is the DUR ratio which is the ratio of the maximum dose and the minimum dose. It has to be as uniform as possible and as low as possible.

Figures 8A, 8B:
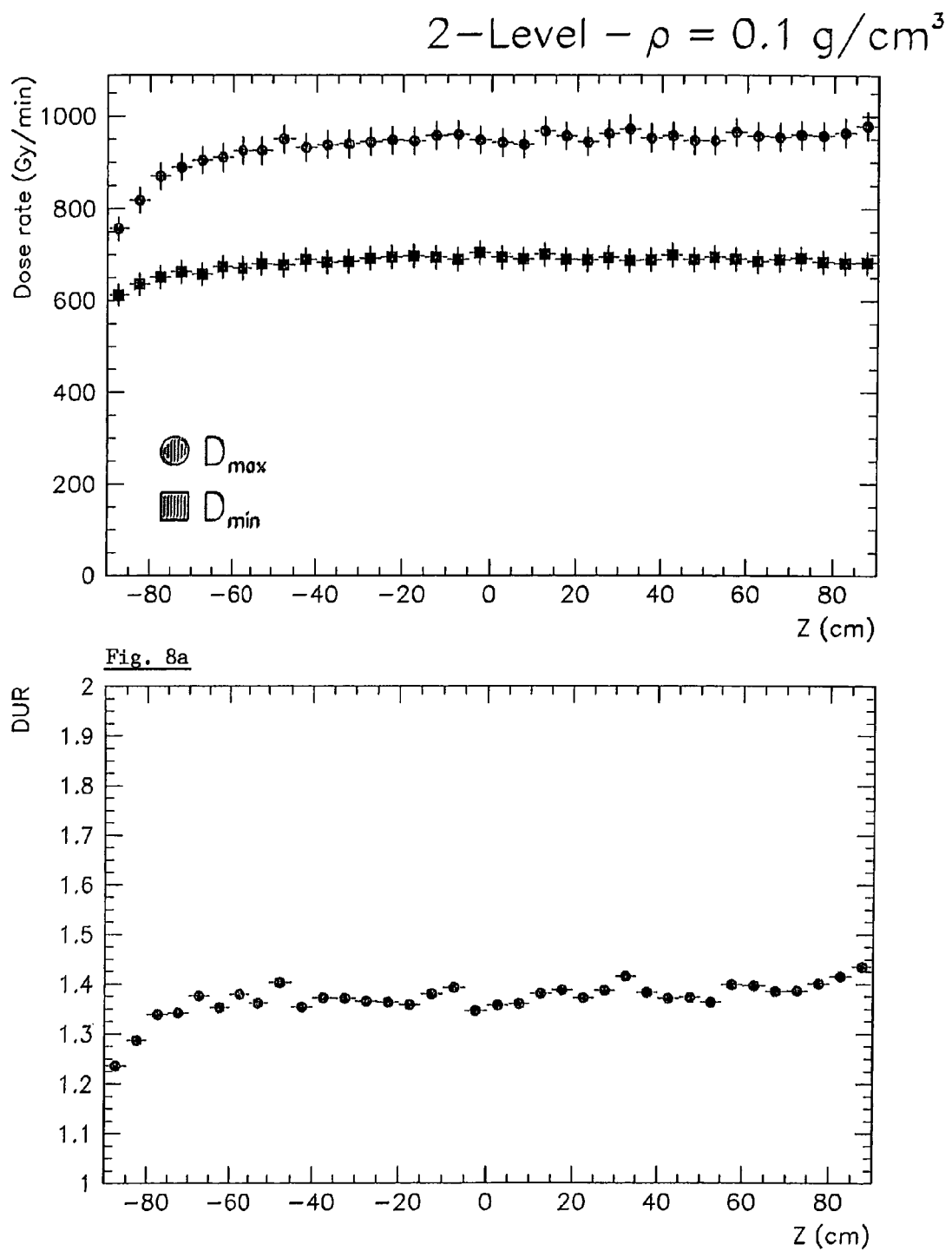
FIGS. 8a and 8b represent the minimum dose rate (Dmin) and the maximum dose rate (Dmax) as well as the DUR ratio, according to the vertical axis of the pallet for a product having a density of 0.1 g/cm$^3$ submitted to the method of the present invention.
Figure 9A:
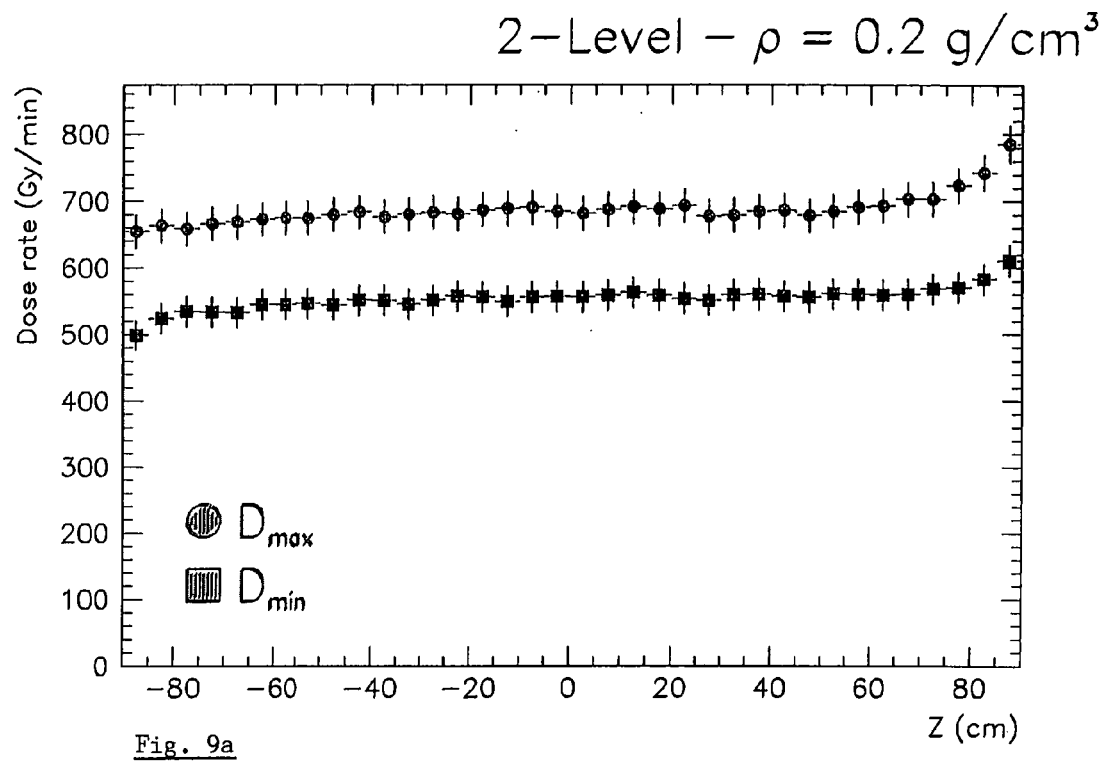
FIGS. 9a and 9b represent the minimum dose rate (Dmin) and the maximum dose rate (Dmax), the DUR ratio, according to the vertical axis of the pallet for a product having a density of 0.2 g/cm$^3$ submitted to the method of the present invention.
Figure 9B:
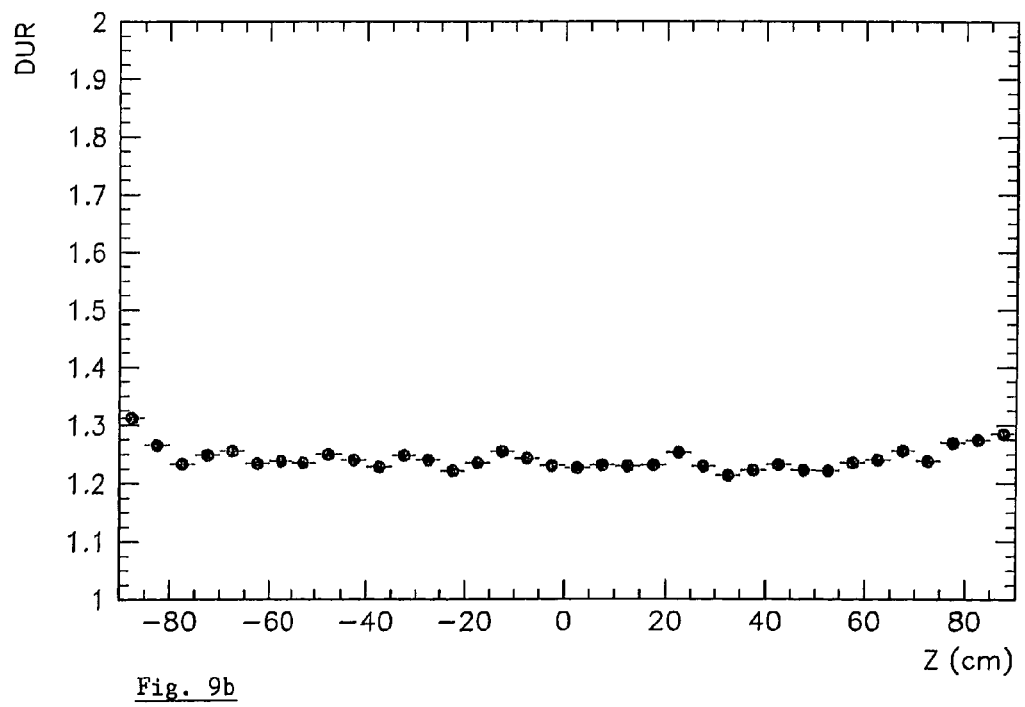
Figure 10A:
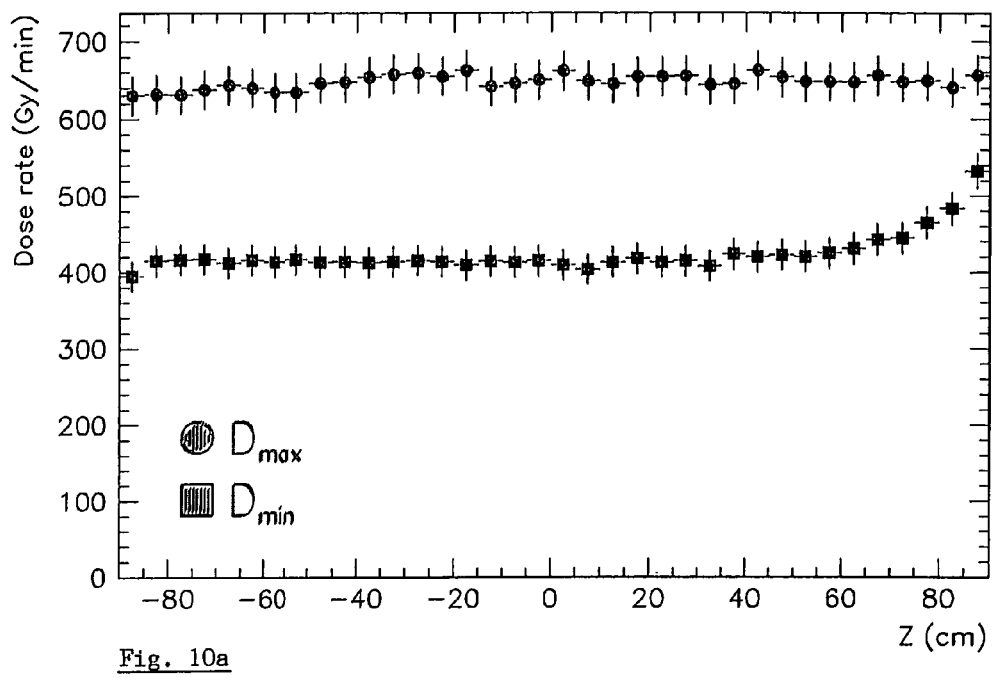
FIGS. 10a and 10b represent the minimum dose rate (Dmin) and the maximum dose rate (Dmax) and the DUR ratio, according to the vertical axis of the pallet for a product having a density of 0.3 g/cm$^3$ submitted to the method of the present invention.
Figure 10B:
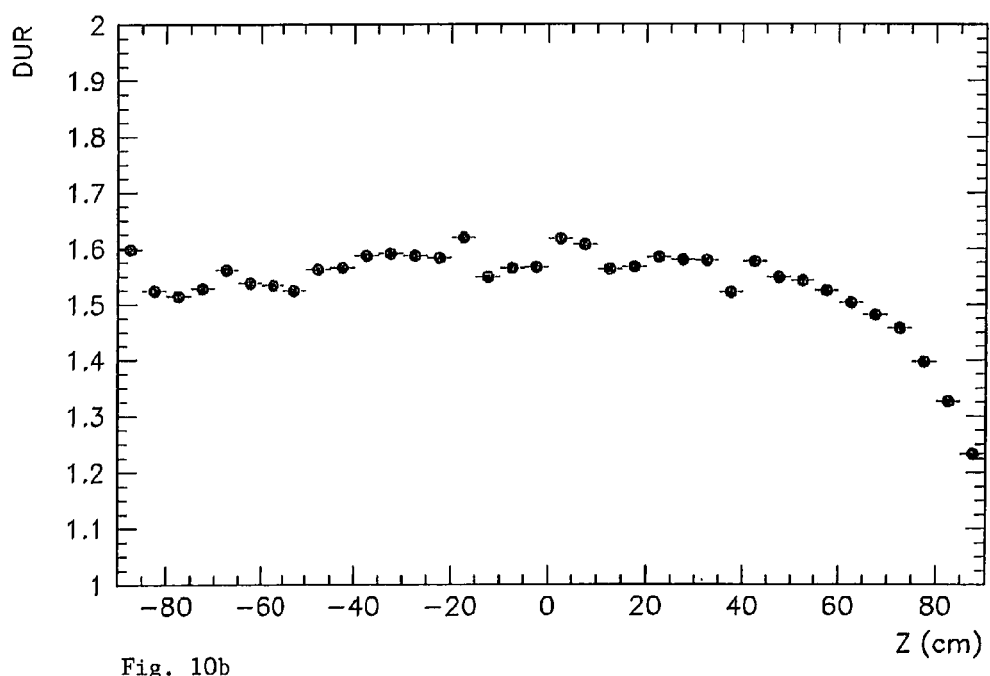

FIG. 8b, FIG. 9b and FIG. 10b represent the DUR ratio for products having a density of 0.1 g/cm$^3$, 0.2 g/cm$^3$, 0.3 g/cm$^3$ respectively.

For products having a very low density, a decrease of the DUR ratio is observed at the bottom of the pallets. However, this effect slowly disappears when increasing the density.

On the other hand, when the density is increasing, an increase of the DUR ratio is observed at the top of the pallets (see FIG. 10b).

Yet, as represented in FIG. 11, if we compare the DUR ratio with the density for a process according to the present invention (two levels process) and for a process performed according to the state of the art (one level process), it is obvious that the DUR ratio is improved (closer to one).

FIG. 12a and FIG. 12b represent a simulation of the behaviour of the photons generated on a conversion target 35 by an electron beam. One will observe that on the left part of the drawings in front of the conversion target 35 the electrons of the electron beam produced by a cyclotron can be considered as having essentially a parallel trajectory. Very few electrons will produce backscattering. The exposure of one set of products placed on only one level will conduct to a rather low throughput (see FIG. 12a) since a non-negligible portion of the X-rays produced is lost. The exposure of two sets of products placed on two superposed levels is represented in FIG. 12b. It is obvious that the rate of lost X-rays has decreased. This can also be observed in FIG. 13.

As represented in FIG. 13, if we compare the throughput according to the density for a process according to the present invention (two levels process) with a process performed according to the state of the art (one level process), it is again obvious that the throughput is radically improved for any density from 0.05 to 0.35 g/cm$^3$. This is particularly put in evidence with FIG. 14 wherein the throughput increase is represented as a percentage.

LIST OF THE NUMERICAL REFERENCES USED IN THE DESCRIPTION 1 irradiation chamber
2/2' conveying means
3/3' set of product(s) (pallet(s) or container(s))
4 X-ray beam source
5 loading portion
6 accumulation portion
7 exposure portion
8 check portion
9 unloading portion
10 reorientation portion
11 exit
12 rotation means
13 reorientation means
14/14'/14"/14'" product pallets
15 square base
16 open column or empty column
17 corner
18 contact point
19 centre of square
20 centre of turntable
30/30' pallets conveyor or turntable
31/31' support or tray of the pallets
32 horn of the electron beam
35 X-ray target

The invention claimed is:

1. A method for irradiating in an irradiation chamber products being stored in the form of pallets or in the form of bulk material in containers with a high energy x-ray beam source, the method comprising:
   placing the products onto two different levels of products, so that a first set of products is placed on an upper level and a second set of products is placed on a lower level;
   irradiating both sets of products during a first period of time by directing the x-ray beam source to the products from about mid-height of the products on the lower level to about mid-height of the products on the upper level;
   switching the products placed on the two levels to make a new arrangement so that the set of products irradiated on the upper level during the first time period are placed on the lower level and the set of products irradiated on the lower level during the first time period are placed on the upper level; and
   irradiating during a second period of time the new arrangement formed of the two switched sets of products by directing the x-ray beam source to the products from about mid-height of the products on the lower level to about mid-height of the products on the upper level.

2. The method according to claim 1, wherein the two different levels are two superposed vertical levels.

3. The method according to claim 1 wherein the total period of irradiation comprises the first period of time and the second period of time and the switching of the two levels occurs in the middle of the total period of irradiation of the products.

4. The method according to claim 1, wherein the products are conveyed before the source with a translation conveyor device.

5. The method according to claim 4, wherein the translation conveyor device comprises two independent parallel sub-devices conveying the products on the two different levels.

6. The method according to claim 1, wherein the products are conveyed before the source with a rotating conveyor device.

7. The method according to claim 6, wherein the rotating conveyor device comprises two independent parallel sub-devices conveying the products on the two different levels.

8. The method according to claim 1, wherein the set of products present on each level comprises one pallet or one container.

9. The method according to claim 1, wherein the set of products present on each level is in the form of a stack of at least several contiguous pallets or containers placed in the same plane.

10. The method according to claim 9, wherein the plane is essentially a horizontal plane.

11. The method according to claim 1, wherein the high energy x-rays are obtained by scanning an electron beam along a conversion target on a height essentially corresponding to a distance comprised between substantially mid-height of the lower level up to substantially mid-height of the upper level.

12. An apparatus for irradiating in an irradiation chamber products being stored in the form of pallets or in the form of bulk material in containers, the apparatus comprising:
- a high energy photon source;
- a conveying device configured to convey the products in front of the photon source and arrange the products in two sets of products, each being placed on a different level, the different levels comprising an upper level and a lower level;
- a transposition device configured to switch the sets of products arranged on each level so that the set of products irradiated on the upper level during the first time period are placed on the lower level and the set of products irradiated on the lower level during the first time period are placed on the upper level, and
- a directing device configured to direct the high energy photon source to the products from about mid-height of the products on the lower level to about mid-height of the products on the upper level.

13. The apparatus according to claim 12, further comprising a directing device configured to direct a photon beam along a height essentially corresponding to a distance comprised between substantially mid-height of the lower level products up to substantially mid-height of the upper level products.

14. A method for irradiating in an irradiation chamber products being stored in the form of pallets or in the form of bulk material in containers with a high energy x-ray beam source, the method comprising:
- placing the products onto two different levels of products so that a first set of products is placed on an upper level on a first horizontal plane and a second set of products is placed on a lower level on a second horizontal plane;
- irradiating both sets of products during a first period of time by directing the x-ray beam source to the products from about mid-height of the products on the lower level to about mid-height of the products on the upper level and holding the first and second horizontal planes stationary during the first time period;
- switching the products arranged on the two levels to make a new arrangement so that the set of products irradiated on the upper level during the first time period are placed on the lower level on the second horizontal plane and the set of products irradiated on the lower level during the first time period are placed on the upper level on the first horizontal plane; and
- irradiating during a second period of time the new arrangement formed of the two switched sets of products by directing the x-ray beam source to the products from about mid-height of the products on the lower level to about mid-height of the products on the upper level and the first and second horizontal planes are held stationary during the second time period,
- wherein the total period of irradiation comprises the first period of time and the second period of time and provides a dose uniformity ratio less than 2.5.

15. The method according to claim 14, wherein the two different levels are two superposed vertical levels.

16. The method according to claim 14, wherein the switching of the two levels occurs in the middle of the total period of irradiation of the products.

17. The method according to claim 14, wherein the products are conveyed before the source with a translation conveyor device comprising two independent parallel sub-devices conveying the products on the two different levels.

18. The method according to claim 14, wherein the products are conveyed before the source with a rotating conveyor device comprising two independent parallel sub-devices conveying the products on the two different levels.

19. The method according to claim 14, wherein the dose uniformity ratio is about 1.

20. The method according to claim 14, wherein the high energy x-rays are obtained by scanning an electron beam along a conversion target on a height essentially corresponding to a distance comprised between substantially mid-height of the lower level up to substantially mid-height of the upper level.

* * * * *